United States Patent
Murphy-Chutorian

[11] Patent Number: 5,891,133
[45] Date of Patent: Apr. 6, 1999

[54] APPARATUS FOR LASER-ASSISTED INTRA-CORONARY TRANSMYOCARDIAL REVASCULARIZATION AND OTHER APPLICATIONS

[75] Inventor: Douglas R. Murphy-Chutorian, Sunnyvale, Calif.

[73] Assignee: Eclipse Surgical Technologies, Inc., Sunnyvale, Calif.

[21] Appl. No.: 627,699

[22] Filed: Mar. 29, 1996

[51] Int. Cl.$^6$ .................................................... A61B 17/36
[52] U.S. Cl. .................................. 606/7; 606/15; 606/17
[58] Field of Search ................................ 606/7, 9, 14–16

[56] References Cited

U.S. PATENT DOCUMENTS

| | | | |
|---|---|---|---|
| 4,658,817 | 4/1987 | Hardy | 128/303.1 |
| 4,950,267 | 8/1990 | Ishihara et al. | 606/12 |
| 5,000,185 | 3/1991 | Yock | 128/662.03 |
| 5,109,830 | 5/1992 | Cho . | |
| 5,125,926 | 6/1992 | Rudko et al. | 606/19 |
| 5,287,861 | 2/1994 | Wilk | 128/898 |
| 5,345,940 | 9/1994 | Seward et al. . | |
| 5,380,316 | 1/1995 | Aita et al. | 606/7 |
| 5,389,096 | 2/1995 | Aita et al. | 606/15 |
| 5,575,787 | 11/1996 | Abela et al. . | |
| 5,607,462 | 3/1997 | Imran . | |

FOREIGN PATENT DOCUMENTS

| | | |
|---|---|---|
| 0515867 A2 | 2/1992 | European Pat. Off. . |
| 0 647 434 A2 | 4/1995 | European Pat. Off. ........ A61B 17/34 |
| 0 834 287 A1 | 4/1998 | European Pat. Off. ........ A61B 17/22 |
| WO 92/10142 A1 | 6/1992 | WIPO . |

OTHER PUBLICATIONS

Deckelbaum, "Cardiovascular Apps. of Laser Tech.", Lasers in Surgery and Medicine, 15:315–341 (1994).
Frazier et al., "Myocard. Revasc. with Las.", Cullen Cardio. Res. Labs., Tx. Heart Inst., Supp. II C vol. 92, No. 9, II–58–65 (Nov. 1, 1995).

*Primary Examiner*—Francis J. Jaworski
*Attorney, Agent, or Firm*—Ray K. Shahani; Janet Kaiser Castaneda; Ilene Lapidus Janofsky

[57] ABSTRACT

Improved methods and apparatuses related to laser-assisted intra-coronary transmyocardial revascularization (ITMR), and more particularly, to improved methods and apparatuses for directing an interventional catheter device, via percutaneous or other entry into the vasculature, for example at the femoral artery, over the aortic arch, through the ascending aorta and over the coronary ostia such that the laser delivery means can be positioned inside a coronary artery and laser energy is used to create a plurality of small channels through the coronary artery into the tissue of the myocardium. An proximal hub portion and method of using it are described, the proximal hub portion adapted for attachment to a central, elongated lumen portion, the proximal hub portion optionally having a plurality of branched extending arms, the sheath and associated branched arms having individual blood loss seals and individually capable of receiving a laser delivery means, visualization or marking means, or other tools. The interventional catheter device has a distal end with, optionally, a guide means for directing an advancing laser delivery or other device to an angle with respect to the central axis of the catheter device, the distal end optionally comprising a radio-opaque portion for visualization via a fluoroscope or other means, the distal end of the catheter device further comprising an ultrasound transducer for visualizing the orientation and firing angles of the catheter device. The methods of use also comprise placing channel opening blockers, such as an angioplasty-type inflatable balloon or an axially compressible, radially expandable stainless steel wire mesh or other material stent in place inside the coronary artery, thereby preventing undesired bleeding from the coronary artery.

54 Claims, 7 Drawing Sheets

APPARATUS FOR LASER-ASSISTED INTRA-CORONARY TRANSMYOCARDIAL REVASCULARIZATION AND OTHER APPLICATIONS

RELATED APPLICATIONS

This application is filed concurrently with U.S. patent application Ser. No. 08/627,701, now U.S. Pat. No. 5,725,521 and U.S. patent application Ser. No. 08/627,704, now U.S. Pat. No. 5,725,523 which applications are expressly incorporated herein in their entirety

FIELD OF THE INVENTION

The present invention relates to a surgical procedure known as laser-assisted intra-coronary transmyocardial revascularization (ITMR), and more particularly, to improved methods and apparatuses for directing a catheter device, via percutaneous or other entry into the vasculature, for example at the femoral artery, over the aortic arch and through the ascending aorta such that a laser delivery means can be positioned inside a coronary artery, laser energy is used to create a plurality of small channels through the coronary artery into the tissue of the myocardium. These methods and apparatuses can be adapted for use in surgical applications throughout the human body or in animals for transmitting laser energy precisely, at predetermined positions and to predetermined depths.

BACKGROUND OF THE INVENTION

FIG. 1 is a schematic view of the human heart. The human heart 10 is a muscular dual pump that beats continuously throughout life sending blood to the lungs and the rest of the body. The interior of the heart consists of four distinct chambers. The septum 12, a thick central muscular wall, divides the cavity into right and left halves. On the right side, the upper half is known as the right atrium 14. Deoxygenated blood from the rest of the body arrives in the right atrium via the vena cava 16, the blood is pumped across a one-way valve known as the tricuspid valve 18 into the lower portion known as the right ventricle 20. From there the blood circulates to the lungs through the pulmonary valve 22 via the pulmonary artery 24 where it is oxygenated by circulation through the alveoli of the lungs (not shown). The blood returns via the pulmonary veins to the left atrium 26 and flows through a second valve, the mitral valve 28 into the left ventricle 30 where it is pumped via the aorta 32 to the rest of the body.

Much of the heart consists of a special type of muscle called myocardium. The myocardium requires a constant supply of oxygen and nutrients to allow it to contract and pump blood throughout the vasculature. The inner surfaces of the chambers of the heart are lined with a smooth membrane, the endocardium, and the entire heart is enclosed in a tough, membranous bag known as the pericardial sac.

The pumping action of the heart has three main phases for each heart beat. Diastole is the resting phase during which the heart fills with blood: while deoxygenated blood is entering the right atrium oxygenated blood is returned from the lungs to the left atrium. During the atrial systole, the two atria contract simultaneously, squeezing the blood into the lower ventricles. Finally, during ventricular systole the ventricles contract to pump the deoxygenated blood into the pulmonary arteries and the oxygenated blood into the main aorta. When the heart is empty, diastole begins again. The electrical impulses which stimulate the heart to contract in this manner emanate from the heart's own pacemaker, the sinoatrial node. The heart rate is under the external control of the body's autonomic nervous system.

FIG. 2 is a schematic view of the coronary arteries on the outer surface of the human heart. Though the heart supplies blood to all other parts of the body, the heart itself has relatively little communication with the oxygenated blood supply. Thus, the two coronary arteries, the right coronary artery 40 and the left coronary artery 42 arise from the aorta 44 beneath the aortic arch 46. Starting at the left coronary osteum 48 and the right coronary osteum 50, respectively, the coronary arteries encircle the heart muscle on either side "like a crown" to supply the heart itself with blood.

Heart disorders are a common cause of death in developed countries. They also impair the quality of life of millions of people restricting activity by causing pain, breathlessness, fatigue, fainting spells and anxiety. The major cause of heart disease in developed countries is impaired blood supply. The coronary arteries, which supply blood to the heart, become narrowed due to atherosclerosis and part of the heart muscle are deprive of oxygen an other nutrients. The resulting ischemia or blockage can lead to angina pectoris, a pain in the chest, arms or jaw due to a lack of oxygen to the heart, or infarction, death of an area of the myocardium caused by the ischemia.

Techniques to supplement the flow of oxygenated blood directly from the left ventricle into the myocardial tissue have included needle acupuncture to create transmural channels (see below) and implantation of T-shaped tubes into the myocardium. Efforts to graft the omentum, parietal pericardium, or mediastinal fat to the surface of the heart had limited success. Others attempted to restore arterial flow by implanting the left internal mammary artery into the myocardium.

Modernly, coronary artery blockage can be relieved in a number of ways. Drug therapy, including nitrates, beta-blockers, and peripheral vasodilatator drugs (to dilate the arteries) or thrombolytic drugs (to dissolve the clot) can be very effective. If drug treatment fails transluminal angioplasty is often indicated-the narrowed part of the artery, clogged with atherosclerotic plaque or other deposits, can be stretched apart by passing a balloon to the site and gently inflating it a certain degree. In the event drug therapy is ineffective or angioplasty is too risky (often introduction of a balloon in an occluded artery can cause portions of the atherosclerotic material to become dislodged which may cause a total blockage at a point downstream of the subject occlusion thereby requiring emergency procedures), the procedure known as coronary artery bypass grafting (CABG) may be indicated. CABG is the most common and successful major heart operation performed, in America alone over 500,000 procedures being performed annually. The procedure takes at least two surgeons and can last up to five hours. First, the surgeon makes an incision down the center of the patient's chest and the heart is exposed by opening the pericardium. A length of vein is removed from another part of the body, typically the leg. The patient is connected to a heart-lung machine which takes over the function of the heart and lungs during the operation. The section of vein is first sewn to the aorta and then sewn onto a coronary artery at a place such that oxygenated blood can flow directly into the heart. The patient is then closed. Not only does the procedure require the installation of the heart-lung machine, a very risky procedure, but the sternum must be sawed through and the risk of infection is enhanced during the time the chest cavity is spread open.

Another method of improving myocardial blood supply is called transmyocardial revascularization (TMR), the creation of channels from the epicardial to the endocardial portions of the heart. The procedure using needles in a form of "myocardial acupuncture" has been experimented with at least as early as the 1930s and used clinically since the 1960s. Deckelbaum. L. I., Cardiovascular Applications of Laser technology, *Lasers in Surgery and Medicine* 15:315–341 (1994). The technique was said to relieve ischemia by allowing blood to pass from the ventricle through the channels either directly into other vessels perforated by the channels or into myocardial sinusoids which connect to the myocardial microcirculation. The procedure has been likened to transforming the human heart into one resembling that of a reptile.

In the reptilian heart, perfusion occurs via communicating channels between the left ventricle and the coronary arteries. Frazier, O. H., Myocardial Revascularization with Laser—Preliminary Findings, *Circulation*, 1995; 92 [suppl II]:II-58-II-65. There is evidence of these communicating channels in the developing human embryo. In the human heart, myocardial microanatomy involves the presence of myocardial sinusoids. These sinusoidal communications vary in size and structure, but represent a network of direct arterial-luminal, arterial-arterial, arterial-venous, and venous-luminal connections. This vascular mesh forms an important source of myocardial blood supply in reptiles but its role in humans is poorly understood.

Numerous studies have been performed on TMR using lasers to bore holes in the myocardium. The exact mechanism by which blood flows into the myocardium is not well understood however. In one study, 20–30 channels per square centimeter were bored into the left ventricular myocardium of dogs prior to occlusion of the arteries. LAD ligation was conducted on both the revascularized animals as well as a set of control animals. Results showed that animals having undergone TMR prior to LAD ligation acutely showed no evidence of ischemia or infarction in contrast to the control animals. After sacrifice of the animals at ages between 4 weeks and 5 months, the laser-created channels could be demonstrated grossly and microscopically to be open and free of debris and scarring.

It is believed that the TMR channels occlude toward the epicardial surface but that their subendocardial section remains patent (unobstructed) and establishes camerosinusoidal connections. It is possible that the creation of laser channels in the myocardium may promote long-term changes that could augment myocardial blood flow such as by inducing angiogenesis in the region of the lased (and thus damaged) myocardium Support of this possibility is reported in histological evidence of probable new vessel formation adjacent to collagen occluded transmyocardial channels. In the case of myocardial acupuncture or boring, which mechanically displaces or removes tissue, acute thrombosis followed by organization and fibrosis of clots is the principal mechanism of channel closure. By contrast, histological evidence of patent, endothelium-lined tracts within the laser-created channels supports the assumption that the lumen of the laser channels is or can become hemocompatible and that it resists occlusion caused by thrombo-activation and/or fibrosis. A thin zone of charring occurs on the periphery of the laser-created transmyocardial channels through the well-known thermal effects of optical radiation on cardiovascular tissue. This type of interface may inhibit the immediate activation of the intrinsic clotting mechanisms because of the inherent hemocompatibility of carbon. In addition, the precise cutting action that results from the high absorption and low scattering of laser energy ($CO_2$, HO, etc.) may minimize structural damage to collateral tissue, thus limiting the tissue thromboplastin-mediated activation of the extrinsic coagulation.

U.S. Pat. No. 4,658,817 issued Apr. 21, 1987 to Hardy teaches a method and apparatus for TMR using a laser. A surgical $CO_2$ laser includes a handpiece for directing a laser beam to a desired location. Mounted on the forward end of the handpiece is a hollow needle to be used in surgical applications where the needle perforated a portion of tissue to provide the laser beam direct access to distal tissue.

U.S. Pat. No. 5,125,926 issued Jun. 30, 1992 to Rudko et al. teaches a heart-synchronized pulsed laser system for TMR. The device and method comprises a device for sensing the contraction and expansion of a beating heart. As the heart beat is monitored, the device triggers a pulse of laser energy to be delivered to the heart during a predetermined portion of the heartbeat cycle. This heart-synchronized pulsed laser system is important where the type of laser, the energy and pulse rate are potentially damaging to the beating heart or it's action. Often, application of laser energy to a beating heart can induce fibrillation or arrhythmia. Additionally, as the heart beats, it's spatial relationship between the heart and the tip of the laser delivery probe may change so that the necessary power of the beam and the required position of the handpiece may be unpredictable.

Finally, U.S. Pat. Nos. 5,380,316 issued Jan. 10, 1995 and 5,389,096 issued Feb. 14, 1995 both to Aita et al. teach systems and methods for intra-operative and percutaneous myocardial revascularization, respectively. The former patent is related to TMR performed by inserting a portion of an elongated flexible lasing apparatus into the chest cavity of a patient and lasing channels directly through the outer surface of the epicardium into the myocardium tissue. In the latter, TMR is performed by guiding an enlongated flexible lasing apparatus into a patient's vasculature such that the firing end of the apparatus is adjacent the endocardium and lasing channels directly through the endocardium into the myocardium tissue without perforating the pericardium layer. These patents do not teach any method for controlling the elongated flexible laser delivery apparatus, nor do they teach methods of visualizing the areas of the heart being lased nor do they teach any method or devices for achieving TMR on surfaces or portions of the heart which are not directly accessible via a sternotomy, mini-sternotomy or via a trocar.

TMR is most often used to treat the lower left chamber of the heart. The lower chambers or ventricles are serviced by the more distal branches of the coronary arteries. Distal coronary arteries are more prone to blockage and resulting heart muscle damage. Roughly 50% of the left ventricle is direct line accessible through a thoracotomy or small incision between the ribs. However, roughly 50% is not direct line accessible and requires either rotating the heart or sliding around to the back side of the heart. Access to the heart is achieved by (1) sliding a device between the heart and pericardial sack which encases the heart, the device likely to have a 45–90 degree bend near the tip, (2) lifting the still beating heart, and (3) penetrating through the direct access side of the heart and/or through the septum of the heart. Lifting the still beating heart is less than desirable especially in patients with lowered heart performance. Furthermore, such manipulation can cause tachycardia (rapid beating of the heart absent undue exertion) fibrillation, arrhythmia or other interruptions in the normal beating cycle.

Thus, broadly, it is an object of the present invention to provide an improved method and device for laser-assisted intra-coronary transmyocardial revascularization (ITMR).

It is a further object of the present invention to provide an improved method or performing ITMR in which channels are created by directing a laser source through the coronary arteries into the myocardium.

It is a further object of the present invention to provide an improved catheter device for performing ITMR which consists of a central lumen, a proximal hub portion at the proximal end of the lumen and a laser delivery means at the distal end of the lumen, optionally along with any of a plurality of additional catheter or surgical tools including visualization means, cutting or resection means, balloons, stents, fluoroscopic marker, ultrasound imaging transmitting or receiving means.

SUMMARY OF THE INVENTION

An interventional catheter device for performing intracoronary laser-assisted transmyocardial revascularization (ITMR) and other surgical applications, the device particularly adapted for introduction of a single-or multi-channel lumen to the vasculature, for access to the coronary ostia, or to other internal region of the human body in general or with visualization means, laser delivery means or other device or system, the interventional catheter device comprising a proximal hub portion for providing direct access to the vasculature or other internal region of the human body from an external position, the proximal hub portion having a predetermined length, the proximal hub portion having a proximal end and a distal end and having a central hollow opening throughout it's length. The device also comprises an elongated lumen, the lumen having a central longitudinal axis, the lumen having a proximal end and a distal end, the lumen having a central hollow opening, the lumen having a tubular sidewall, the proximal end attached to the distal end of the proximal hub portion such that the central hollow opening of the proximal hub portion is contiguous with and aligned with the central hollow opening of the lumen, the lumen having a predetermined length and shape so as to extend through the vasculature of the patient from the distal end of the proximal hub portion to a position adjacent predetermined tissue, wherein visualization means, laser delivery means and other devices or systems can be placed inside the coronary arteries or other internal body region via the proximal hub portion of the interventional catheter device to perform ITMR or other medical procedures. The device also comprises a laser delivery means guide means, the guide means disposed adjacent the distal end of the lumen, the guide means positioned to deflect the distal end of a laser delivery means extendable through the lumen, such that laser energy is delivered at an angle to the central longitudinal axis of the lumen. In a preferred embodiment the lumen is a multi-channel lumen, each of the lumen channels extending axially through the length of the lumen. In a preferred embodiment the proximal hub portion has one or more branched arms extending therefrom, the branched arms each having a predetermined length, the hollow arms each having a proximal end and a distal end, each branched arm having a central hollow opening throughout it's length, the central hollow opening of each branched arm extending into the central hollow opening of the proximal hub portion thereby permitting communication between and through the central hollow openings of the branched arms and the central hollow opening of the proximal hub portion. In a preferred embodiment the central hollow openings of the branched arms extending from the proximal hub portion do not communicate with each other or with the central hollow opening of the proximal hub portion but rather extend to the distal end of the proximal hub portion and connect with the lumen such that the central hollow openings of the branched arms as well as of the proximal hub portion itself are contiguous and aligned with the central hollow opening of the lumen. In a preferred embodiment the lumen is a multi-channel lumen, each of the lumen channels extending axially throughout the length of the lumen, each of the lumen channels in direct communication with one or more of the central hollow openings such that access to the ostia of the coronary or other internal regions of the human body can be had with a plurality of devices or for a plurality of purposes. In a preferred embodiment there is a moveable guidewire, the guidewire capable of being introduced into the catheter device via a central hollow opening of either the proximal hub portion or a branched arm thereof and extended therethrough to a point adjacent the distal end of the lumen. In a preferred embodiment there is a visualization means, the visualization means capable of being introduced into the catheter device via a central hollow opening of either the proximal hub portion or a branched arm thereof and extended therethrough to a point adjacent the distal end of the lumen. In a preferred embodiment there is a blood loss seal, the blood loss seal disposed between the proximal end and the distal end of the proximal hub portion, thereby preventing the undesired loss of blood from the vasculature through the lumen and the central hollow opening. In a preferred embodiment there are a plurality of blood loss seals, the blood loss seals disposed between the proximal ends and the distal ends of the proximal hub portion and the branched arms thereof thereby preventing undesired loss of blood from the vasculature or other region of the human body through the catheter device. In a preferred embodiment there is a laser delivery means, the laser delivery means having a distal end and a proximal end, the laser delivery means axially movable within the catheter device, the laser delivery means capable of being introduced into the catheter device via a central hollow opening of either the proximal hub portion or a branched arm thereof and extended therethrough, the distal end of the laser delivery means positioned adjacent the distal end of the lumen, the laser delivery means capable of delivering laser energy from it's distal end through the distal end of the lumen. In a preferred embodiment the distal end of the laser delivery means has a predetermined, radiused or other non-sharp cornered shape to prevent binding on the laser delivery means guide means or cam surface thereof. In a preferred embodiment there is a laser delivery means, the laser delivery means having a distal end and a proximal end, the laser delivery means axially fixed within the catheter device, the distal end of the laser delivery means positioned adjacent the distal end of the lumen, the laser delivery means capable of delivering laser energy from it's distal end through the distal end of the lumen. In a preferred embodiment there is a plurality of laser delivery means, the plurality of laser delivery means each having a distal end and a proximal end, the plurality of laser delivery means each axially movable within the catheter device, the plurality of laser delivery means capable of being introduced into the catheter device via a central hollow opening of either the proximal hub portion or a branched arm thereof and extended therethrough, the distal ends of the plurality of laser delivery means positioned adjacent the distal end of the lumen, the plurality of laser delivery means capable of delivering laser energy through the distal end of the lumen from their distal ends. In a preferred embodiment the distal ends of the laser delivery means have predetermined, radiused or other non-sharp cornered shapes to prevent binding on the laser delivery means guide means or cam surface thereof. In a preferred embodiment there is a plurality of laser delivery means, the plurality of laser delivery means each having a distal end and a proximal end, the plurality of laser delivery means each axially fixed within the catheter device, the distal ends of the plurality of laser delivery means positioned adjacent the distal end of the lumen, the plurality laser delivery means capable of delivering laser energy from their distal ends through the distal end of the lumen. In a preferred embodiment the laser delivery means guide means comprises a cam surface, the cam surface having a predetermined shape such that visualization means, laser delivery means or other device or system introduced at the proximal end of the lumen and extended through the lumen will be deflected at an angle to the central axis of the lumen. In a preferred embodiment the cam surface is coated with a low-friction coating. In a preferred embodiment the laser delivery means guide means comprises an opening in the sidewall of the lumen adjacent the distal end of the lumen to direct the distal end of the laser delivery device at an angle to the central axis of the lumen. In a preferred embodiment the laser delivery means guide means comprises a plurality of openings in the sidewall of the lumen adjacent the distal end of the lumen to direct the distal end of the laser delivery device at an angle to the central axis of the lumen. In a preferred embodiment there is a radio-opaque material disposed near the distal end of the interventional device, the radio-opaque material useful for assisting in the visualization of the device and manipulations thereto via a fluoroscope or other suitable viewing means. In a preferred embodiment a radio-opaque material marking band is placed adjacent the distal end of a laser delivery means. In a preferred embodiment there is an ultrasound transducer disposed near the distal end of the interventional device, the ultrasound transducer useful for assisting in the visualization of the device and manipulations thereto via an ultrasound imaging system or other suitable viewing means. In a preferred embodiment the ultrasound transducer comprises a piezoelectric crystal. In a preferred embodiment the ultrasound transducer comprises a plurality of piezoelectric crystals arranged in a predetermined orientation. In a preferred embodiment the laser delivery means comprises a spring member to deflect the distal end of the laser delivery means in a predetermined direction at an angle to the central axis of the elongated lumen. In a preferred embodiment the laser delivery means comprises a fiber bundle and the spring member is disposed within the matrix of fibers comprising the fiber bundle.

A method of performing intra-coronary laser-assisted transmyocardial revascularization (ITMR) and other similar surgical procedures, the method especially useful for revascularizing preselected portions of the myocardium by channeling from the inside of the coronary arteries directly through the sidewall of the coronary arteries into the myocardium, the method comprising the following steps: (a) introducing an elongated hollow lumen into the vasculature; (b) positioning a laser delivery means, by means of a lumen, inside the coronary artery adjacent preselected portions of myocardium by extending the laser delivery means into the coronary artery; and (c) delivering laser energy through the distal end of the laser delivery means through the sidewall of the coronary artery such that a perforation is created in the sidewall of the coronary artery through to and into preselected portions of myocardium a predetermined distance. In a preferred embodiment the laser delivery means is positioned inside the coronary artery by passing it over the aortic arch, down the ascending aorta, and over the right or the left coronary osteum into the subject coronary artery. In a preferred embodiment the method further comprises the following step: (d) advancing the distal end of the laser delivery means through the perforation in the sidewall of the coronary artery into the myocardium while continuing to deliver laser energy such that the distal end of the laser delivery means is advanced to a position adjacent the distal end of the channel created thereby. In a preferred embodiment the method further comprises the following step: (e) placing a channel blocking means from within the coronary arteries occluding the perforation in the sidewall of the coronary artery. In a preferred embodiment the channel blocking means comprises an expandable stent. In a preferred embodiment the channel blocking means comprises an expandable balloon. In a preferred embodiment the method further comprises the following step: (f) orienting the distal end of a laser delivery means so as to deliver laser energy to the myocardium in a direction lying at a predetermined angle to the central axis of the coronary artery. In a preferred embodiment orientation is carried out using visualization. In a preferred embodiment orientation is carried out using an ultrasound transducer in conjunction with an ultrasound imaging system.

A method of performing intra-coronary laser-assisted transmyocardial revascularization (ITMR) and other similar surgical procedures, the method especially useful for revascularizing preselected portions of the myocardium by channeling from the inside of the coronary arteries directly through the sidewall of the coronary arteries into the myocardium, the method comprising the following steps: (a) introducing an elongated hollow lumen into the vasculature; (b) positioning a laser delivery means, by means of a lumen, inside the coronary artery adjacent preselected portions of myocardium by extending the laser delivery means into the coronary artery; (c) advancing the distal end of a catheter or surgical device through the sidewall of the coronary artery such that a perforation is created in the sidewall of the coronary artery through to the myocardium; (d) advancing the distal end of a laser delivery means through the perforation in the sidewall of the coronary artery into the myocardium while delivering laser energy from the distal end of the laser delivery means such that the distal end of the laser delivery means is advanced to a position adjacent the distal end of the channel created thereby. In a preferred embodiment positioning of the laser delivery means is carried out using an ultrasound transducer in conjunction with an ultrasound imaging system.

Numerous other advantages and features of the present invention will become readily apparent from the following detailed description of the invention and the embodiments thereof, from the claims and from the accompanying drawings in which the details of the invention are fully and completely disclosed as a part of this specification.

DETAILED DESCRIPTION OF THE PREFERRED EMBODIMENT

Figure 1:
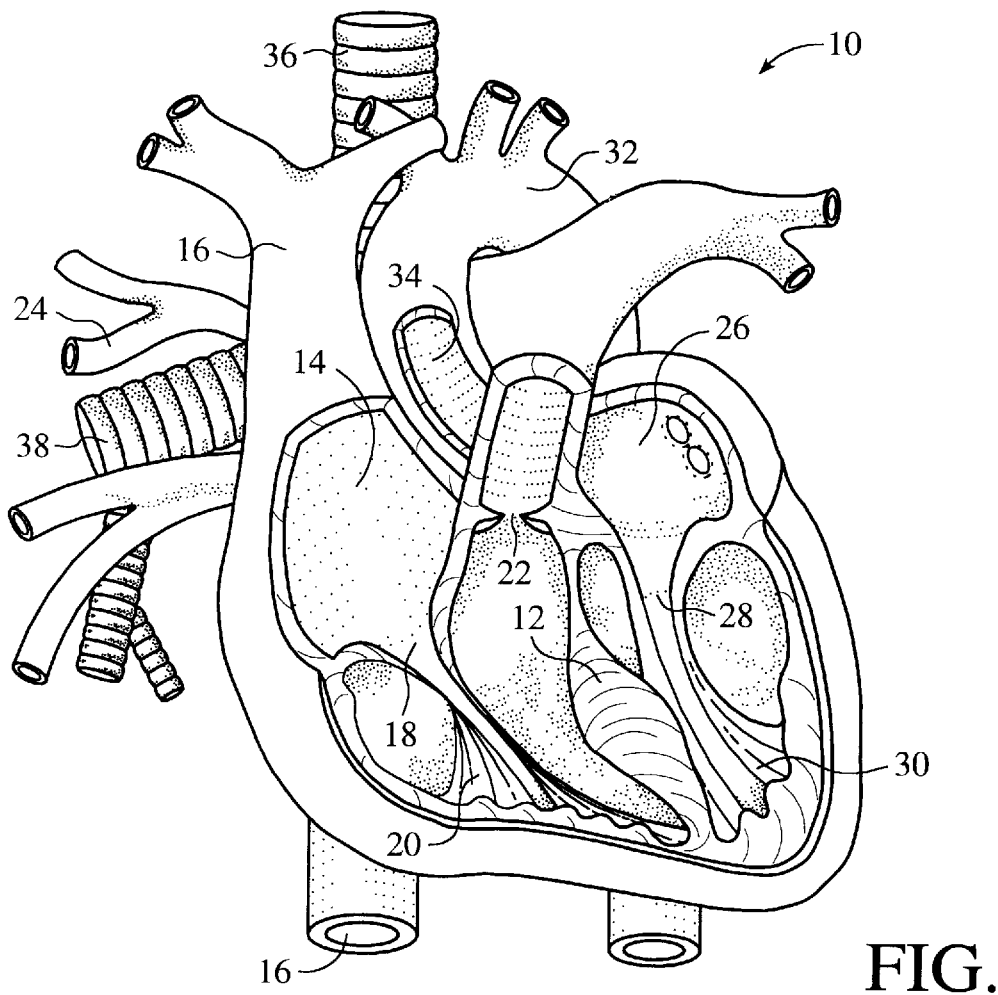
FIG. 1 is a schematic view of the human heart.
Figure 2:
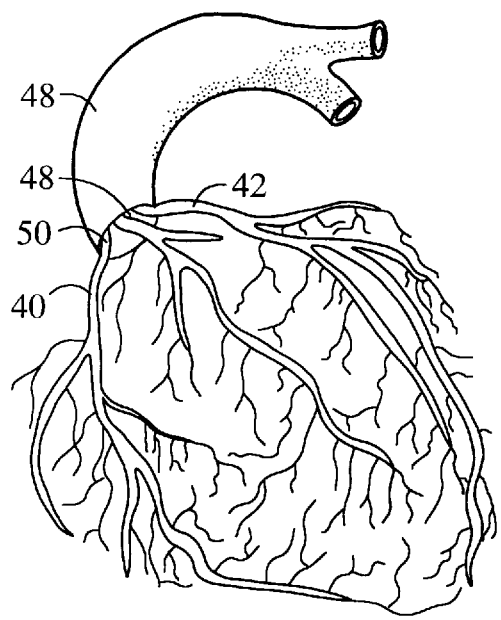
FIG. 2 is a schematic view of the coronary arteries on the outer surface of the human heart.
Figure 3A:
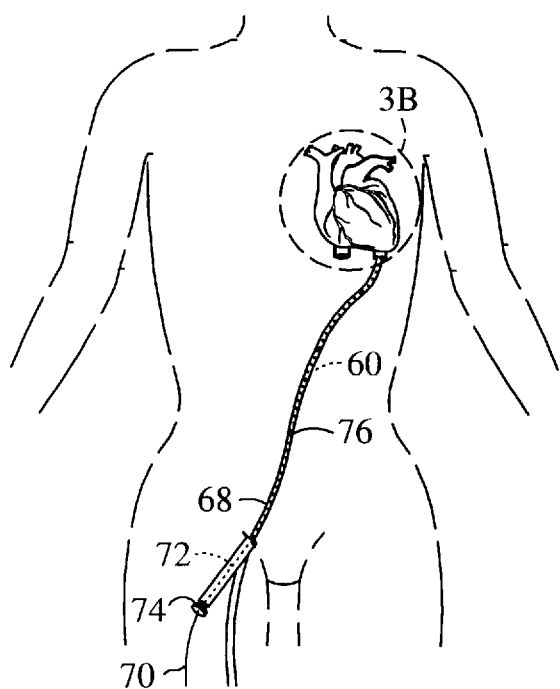
FIGS. 3A–3C are perspective views of a preferred method of performing ITMR or other procedure using a preferred embodiment of an interventional catheter device of the present invention.
Figure 3C:
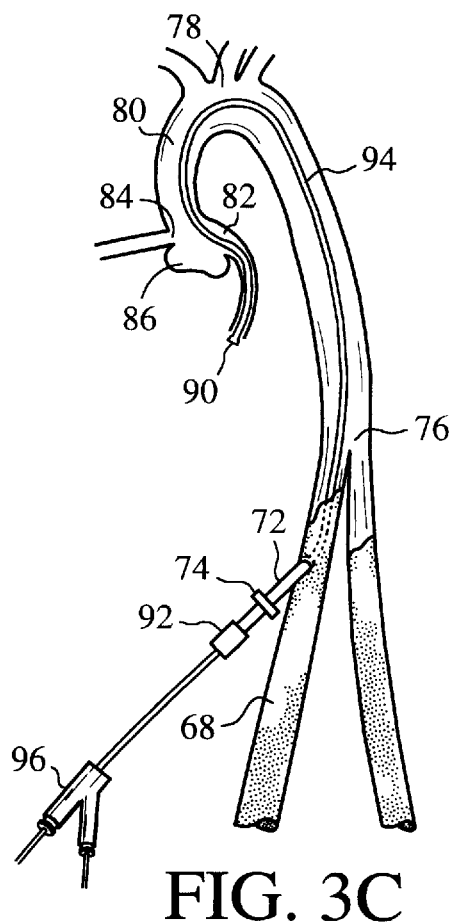
Figure 3B:
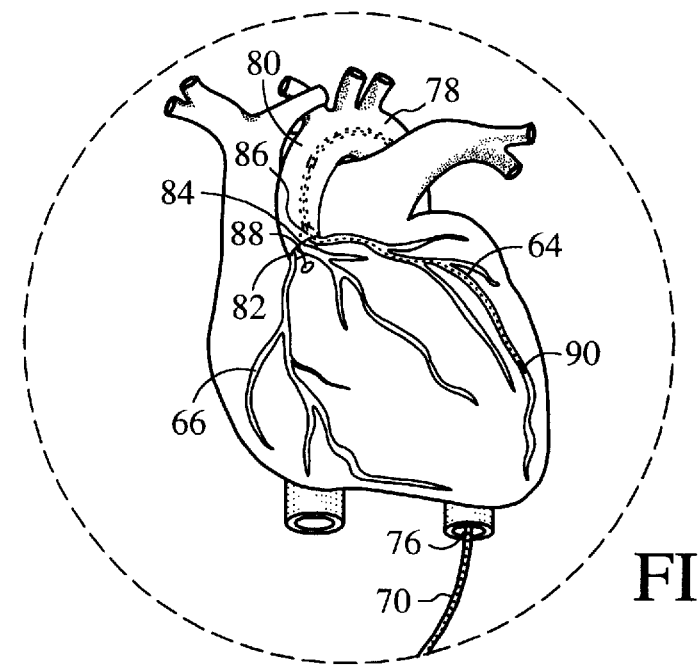

FIGS. 3A–3C are perspective views of a preferred method of performing ITMR or other procedure using a preferred embodiment of an interventional catheter device of the present invention. The vascular system 60 includes arteries which carry oxygenated blood from the left ventricle, through the aorta 62 and throughout the body. Veins transport de-oxygenated blood back to the right atrium. Entry into the vasculature via the femoral artery is practiced widely for numerous applications, given a number of factors including its relatively large size, proximity to the skin, and direct access to the left ventricle and the left and the right coronary arteries, 64 and 66 respectively. The surgeon will gain access typically in the groin area using a standard needle to probe and find the femoral artery 68. The location will be confirmed when a flash of blood spurts back up the needle indicating arterial blood pressure.

A guide wire 70 is threaded through the needle into the artery and the needle is removed. The guidewire serves as a track or rail for the catheter to run on. Typical guidewires can run between about 0.010 and 0.06 inches in diameter, with 0.014 and 0.018 inches diameter typical sizes for coronary artery applications. They may have soft bendable tips of coiled wire or plastic and a more rigid shaft of tapered ground stainless steel or other suitable material for push and torque transmission. The procedure for introducing catheters over guidewires in this manner is well known.

A plastic tube or introducer sheath 72 is introduced over the guidewire. A blood loss seal 74 is generally used on an introducer sheath to prevent the loss of blood from the artery through the sheath. Once in place, a suitable guidewire (the same as initially used following insertion of the needle or another) will be pushed into the femoral artery, up the descending aorta 76, over the aortic arch 78 and down the ascending aorta 80. The left and the right coronary ostia 82 and 84 are the coronary artery origins opening from the aortic cusp 86 of the ascending aorta (on top of the heart just above the aortic valve) into the left and right coronary arteries, respectively. The guide wire, possibly using a guiding sleeve or other guiding means, can be directed into the ostia and down the coronary artery. The guiding sleeve is a thin walled sleeve with a preformed curve shape. Once the curve shape engages the ostium of choice, it provides a type of arterial conduit for the guide wire or other device extending therethrough into the coronary artery. Guiding means can also refer to other types of guiding catheters, tips or fittings used to locate and engage the coronary ostia The surgeon may use a fluoroscope to help direct the tip 90 of the guidewire where needed. Since the guidewire is more torqueable, pushable and flexible, it will lead the way.

Once the guidewire is in place, or as it is being positioned, a guiding catheter 92 is inserted. This guiding catheter has a central lumen 94 which extends all the way to adjacent the sites in the coronary artery to be channeled through into the myocardium. An interventional catheter device 96 is then inserted or installed inside the guiding catheter and pushed through the guiding catheter into the vasculature and heart or other body region. This interventional device may include laser delivery means, visualization means, etc., and will be more fully described below. It will be understood that the guiding catheter/interventional catheter combination system described herein may be altered in various ways. For example, the guiding catheter could be laminated and the interventional catheter could be introduced directly over and along the guidewire.

Figure 4:
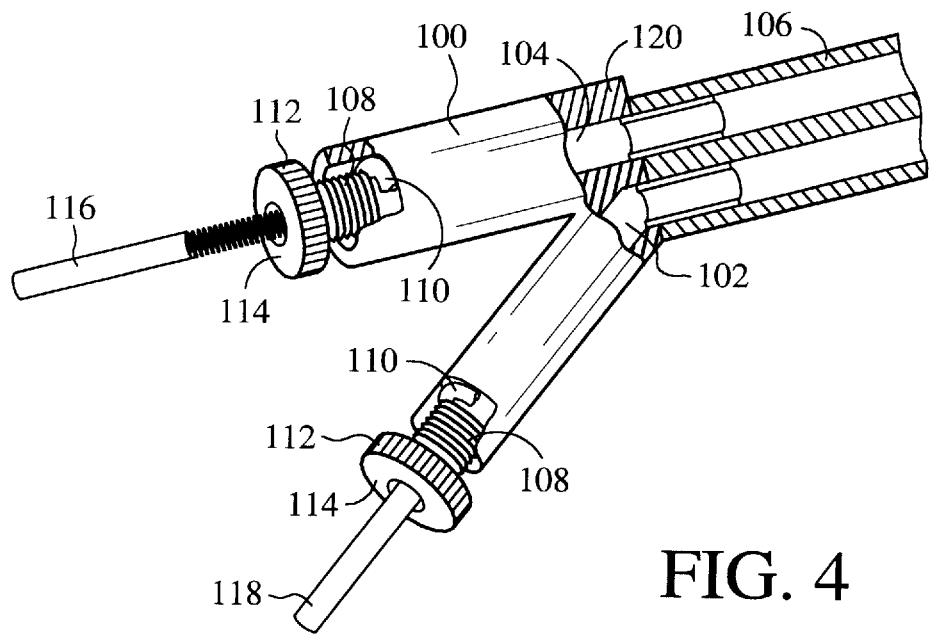
FIG. 4 is a cross section view of a preferred embodiment of the proximal hub of an interventional catheter device of the present invention.

FIG. 4 is a cross section view of a preferred embodiment of the proximal hub 100 of an interventional catheter device of the present invention. The proximal hub can be made of a rigid or semi-flexible material, with various types of plastic or rubber or other materials being suitable. A preferred embodiment of the device has a plurality of arms 102 in addition to its central channel 104. Contiguous with the central channel and those of the plurality of arms, a main lumen 106 extends. Each channel contiguous with the main lumen may be equipped with a blood loss seal 108. A preferred embodiment of the blood loss seal comprises a deformable O-ring 110 and a tightening means such as a threaded end cap 112. Each arm as well as the central channel have proximal ends 114 through which access to the distal end of the main lumen is achieved. In FIG. 4 a guidewire 116 and a laser delivery means 118 such as an optical fiber are shown adjacent proximal ends of the proximal hub of the catheter device. The distal end 120 of the hub is bonded to the main lumen.

It will be understood that the branched arms of the proximal hub portion of the catheter device can be used to introduce any of a plurality of devices into the vasculature or other body region. Visualization means, including fiber bundles or other viewing apparatus, balloonoscopy viewing devices, fluorescent markers, etc. can all be used with the catheter device of the present invention.

Figure 5A:
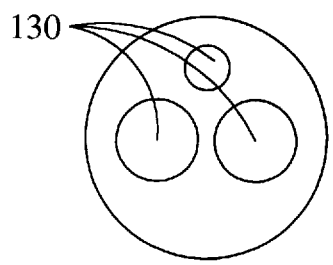
FIG. 5A is a cross section view of a preferred embodiment of a three-channel lumen of a catheter device of the present invention.
Figure 5B:
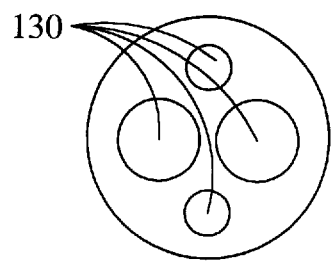
FIG. 5B is a cross section view of a preferred embodiment of a four-channel lumen of a catheter device of the present invention.

FIG. 5A is a cross section view of a preferred embodiment of a three-channel lumen of a catheter device of the present invention. FIG. 5B is a cross section view of a preferred embodiment of a four-channel lumen of a catheter device of the present invention. The plurality of channels 130 serve to provide access to the heart or other internal position in the body with one or more independently operated catheter, surgical or other interventional devices. It will be apparent to those skilled in the art that multi-channel lumen construction can be made of various materials, including polymeric materials, metals, etc. These lumens are typically extruded and can have essentially any possible number of channels, the individual channels themselves as well as the outer surface having any predetermined cross-sectional shape such as circular, hemispherical, crescent shaped, etc.

Figure 6A:
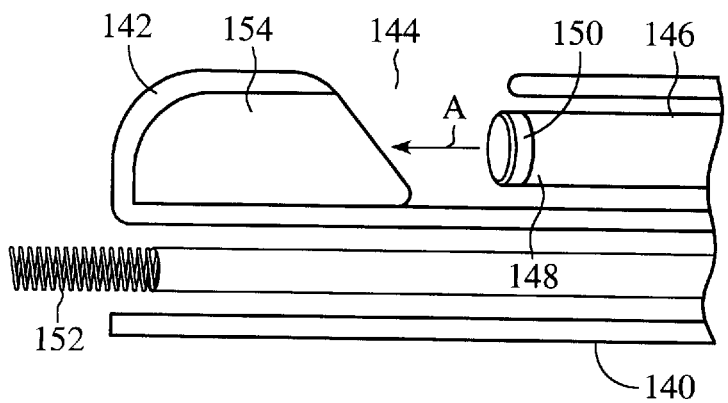
FIG. 6A is a graphic representation of a preferred method of performing ITMR or other suitable procedure showing a first position of a laser delivery means inside a preferred embodiment of an interventional catheter device of the present invention.

FIG. 6A is a graphic representation of a preferred method of performing ITMR or other suitable procedure showing a first position of a laser delivery means inside a preferred embodiment of an interventional catheter device of the present invention. As discussed above, preferred embodiments of the multi-channel lumen used with the catheter device and methods of the present invention are used in the following manner. Once the guidewire is positioned properly inside of a coronary artery adjacent an area of the myocardium to be revascularized, an interventional catheter or other catheter device is introduced and placed appropriately. A preferred embodiment of an interventional catheter 140 of the present invention has a distal end 142. Adjacent the distal end of the catheter device, a laser delivery port 144 is positioned. This port allows laser energy from an advancing laser delivery means 146 to exit the catheter device. The laser delivery means, a fiber optic or other waveguide, is shown in a retracted position. The laser delivery means is moved in the direction A to advance the distal end 148 of the laser delivery means toward the port. On the distal end of the laser delivery means, a curved or chamfered profile 150 is made. This curved or smoothed shoulder, if given a slight radius, will aid the laser delivery means in deflecting at the cam surface more easily and will resist chipping and catching on other surfaces, grooves, etc. in the system. The guidewire 152 is shown extending from the distal end of the catheter device. Optionally, the distal end of the catheter device may be equipped with a radio-opaque tip 154 or other marker/signal transducer in the tip such that the position of the catheter device can be detected or visualized, e.g., by using a fluoroscope or other detector.

It will be understood that "firing window" in addition to "laser delivery port", "distal end of the lumen" and other terms can be used to describe the end portion of a catheter device from which intervention can occur. In the case of a laser delivery means, the distal laser delivering end would extend just outside the port or window and deliver energy to the tissue or area of interest. Further, the distal end of the lumen may have an opening on the end or the side adjacent the very end. All of these openings, if only one or if more than one, will be considered to lie at or near the distal end of the lumen.

Figure 6B:
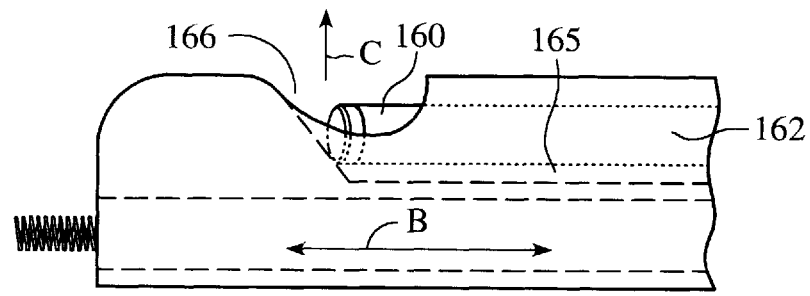
FIG. 6B is a graphic representation of a preferred method of performing ITMR or other suitable procedure showing an intermediate position of a laser delivery means inside a preferred embodiment of an interventional catheter device of the present invention.

FIG. 6B is a graphic representation of a preferred method of performing ITMR or other suitable procedure showing an intermediate position of a laser delivery means inside a preferred embodiment of an interventional catheter device of the present invention. In this embodiment, the catheter device is placed with its distal end adjacent tissue to be revascularized, and the distal end 160 of the laser delivery means 162 is in position adjacent the distal end 164 of the lumen 165. The laser delivery means will be deflected at the cam surface 166 at the distal end of the catheter device. In a preferred embodiment, an angle-firing laser delivery means is placed movably inside the catheter device. In this embodiment, once the firing tip of the angle-firing laser delivery means is positioned just inside the laser delivery port at the distal end of the catheter device, being moved in direction B, laser energy can be delivered directly through the port to tissue for aiming, visualization, general ablation of tissue or creation of channels in the heart, and directed outward in a predetermined direction C. The same result is achieved by placing a reflective surface in the distal end of the catheter device so as to reflect laser energy directed onto the reflective surface out the laser delivery port perpendicularly.

Figure 6C:
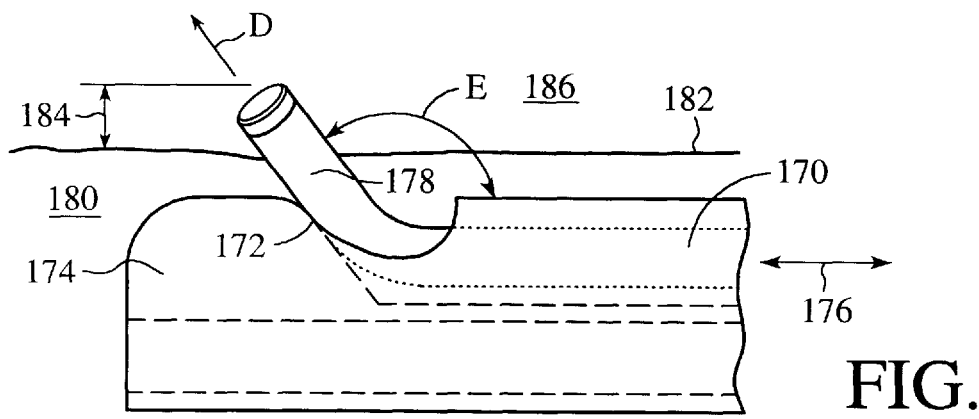
FIG. 6C is a graphic representation of a preferred method of performing ITMR or other suitable procedure showing an operating position of a laser delivery means inside a preferred embodiment of an interventional catheter device of the present invention.

FIG. 6C is a graphic representation of a preferred method of performing ITMR or other suitable procedure showing an operating position of a laser delivery means inside a preferred embodiment of an interventional catheter device of the present invention. In FIG. 6C the distal end of the laser delivery means 170 has been advanced in the direction D after the distal end of the laser delivery means comes into contact with the cam surface 172. A groove, ramp or other laser delivery means guide means 174 is part of the cam surface, either an installed fitting or tip or integral with the distal end of the lumen, on the distal end of the catheter device. The function of this groove, ramp or other laser delivery means guide means is to deflect the distal end of the laser delivery means in a predetermined direction. The laser energy fires in direction D forming an angle E with the central axis 176 of the lumen. It will be understood that the deflected portion 178 can penetrate through the coronary artery 180 and through the coronary artery/myocardium interface 182, if at all, a predetermined distance 184 into the myocardium 186. The laser delivery means can be pushed into the channel and moved back and forth to create a very narrow channel of a predetermined depth. In the preferred embodiment, the laser energy would be directed at an angle other than perpendicular to the central axis of the laser delivery means and catheter device lumen.

In a preferred embodiment, the cam surface or other laser delivery means guide means will be coated with an anti-or low-friction coating. Coating materials might include teflon, paralyene, etc. and will be known to those skilled in the art. The purpose of the low-friction coating is to prevent as much frictional interference as possible while the surgeon is operating the distal end of a laser delivery means or other inserted device. Though sometimes the friction will be important to a certain process or device used within the catheter device, reducing the frictional loss at the cam surface will often be desirable.

A preferred embodiment of the method of the present invention utilizes a fiber optic as a laser delivery means. The fiber could be replaced with a fiber bundle as well. The distal tip of the fiber or bundle or other laser energy waveguide can lase a perforation in the coronary artery wall into the myocardium. Alternatively, the tip of the fiber or bundle can be used to mechanically pierce through the artery. In this embodiment, once the distal tip is buried in the myocardium, pulsed or continuous lasing will create discrete channels, optionally pushing the fiber forward into the hole as it is being created.

Figure 6D:
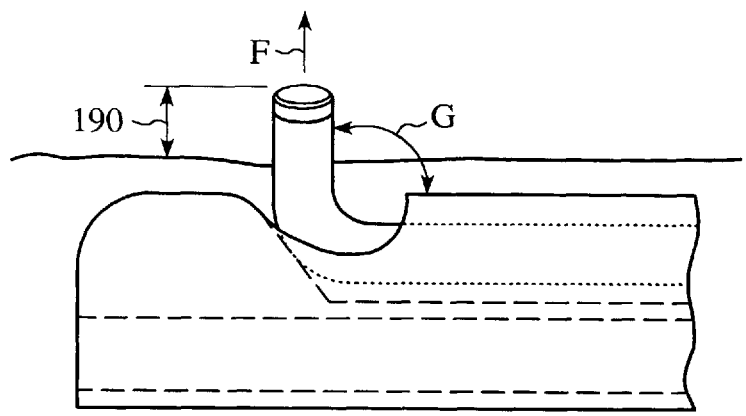
FIG. 6D is a graphic representation of a preferred method of performing ITMR or other suitable procedure showing an operating position of a laser delivery means inside a preferred embodiment of an interventional catheter device of the present invention.

FIG. 6D is a graphic representation of a preferred method of performing ITMR or other suitable procedure showing an operating position of a laser delivery means inside a preferred embodiment of an interventional catheter device of the present invention. In FIG. 6D the laser energy fires in direction F such that angle G is formed between laser delivery means distal end and the central axis. The distal end of the catheter device extends a predetermined distance 190 into the myocardium. It will be apparent to those skilled in the art that the precise orientation and shape of the resulting channels created in the myocardium will be largely dependent on the angle at which the laser delivery means' distal end is deflected or bent. The type of laser delivery means, the diameter of optical fiber or other waveguide, the angle of divergence and other considerations will be important in the method of the present invention. In the present drawing, the laser energy will be directed essentially perpendicularly to the central axis of the laser delivery means and associated distal end of the catheter device.

Figure 7:
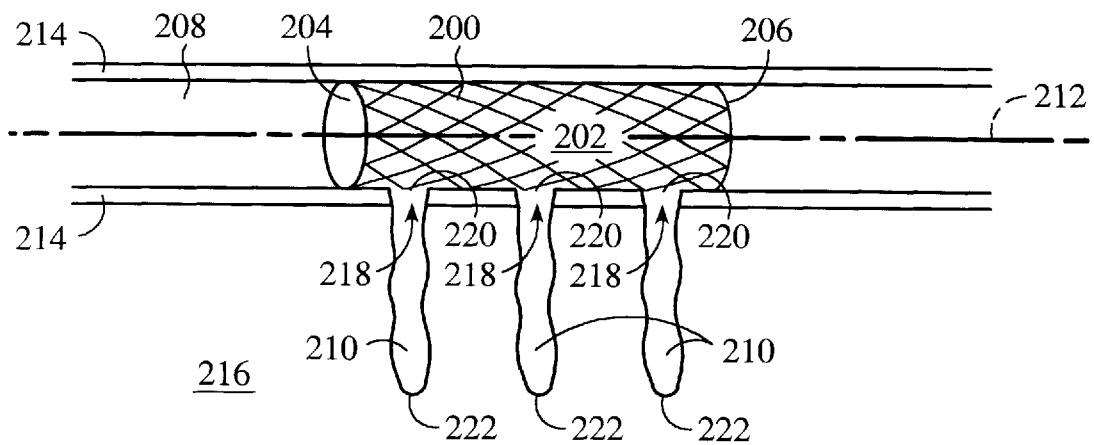
FIG. 7 is a graphic representation of a stent device placed inside the coronary artery over the channel holes of a plurality of channels created using preferred embodiments of devices and methods of the present invention.

FIG. 7 is a graphic representation of a stent device placed inside the coronary artery over the channel holes of a plurality of channels created using preferred embodiments of devices and methods of the present invention. Any device to serve as a channel blocking means to occlude the proximal openings of the channels made in the sidewall of the coronary artery will aid in hemostasis (prevent excess bleeding). A preferred embodiment of a stent 200 is comprised of a stainless steel wire mesh portion 202 in the shape of a short cylinder. The distal end 204 and the proximal end 206 are placed within the coronary artery 208 such that the mesh portion covers one or more radially extending channels 210. It will be understood that regardless of the orientation of the channels with respect to the axis 212 of the coronary artery, they will originate at the inside of the sidewall 214 of the coronary artery and penetrate the myocardium tissue 216. Once the stent is placed over the coronary artery perforations or channel openings 218, the stent can be expanded or otherwise secured into place if necessary. This could be by an expanding means such as a balloon or a pusher system to compress the stent axially thereby increasing it's diameter. Sutures or tissue adhesive could also be used. Stents are designed for the fast deposition and over growth of endothelial cells. Once overgrown they no longer represent a foreign body response threat in the blood stream and are essentially ignored thereafter by the body. The channels into the myocardium themselves each have a proximal end 220 and a distal end 222.

Figure 8A:
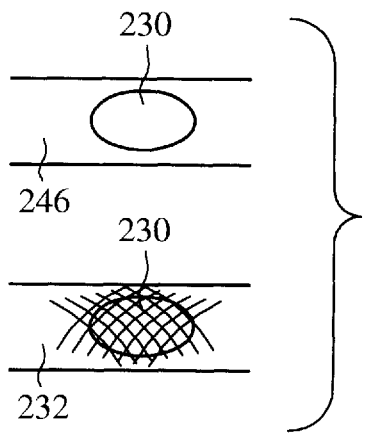
FIG. 8A is a plan view of a coronary artery with a channel created therein both before and after placing a stent device, all by means of devices and methods of the present invention.

FIG. 8A is a plan view of a coronary artery with a channel created therein both before and after placing a stent device, all by means of devices and methods of the present invention. In FIG. 8A a profile of the channel opening 230 is shown both before and after the stent 232 is placed. Once the stent is placed covering the channel openings created by the laser energy, it will prevent bleeding from the coronary artery directly and uncontrollably into the myocardium tissue or elsewhere. The stent will also maintain a channel through the coronary artery, a contributing factor to the efficacy of the present methods and devices.

Figure 8B:
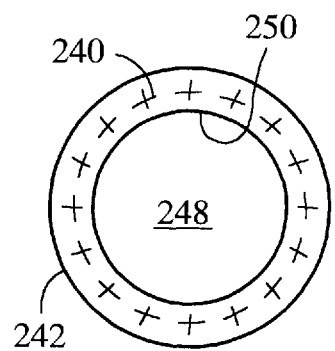
FIG. 8B is a cross section view of a stent device placed by means of devices and methods of the present invention.

FIG. 8B is a cross section view of a stent device placed by means of devices and methods of the present invention. This view clearly shows the mesh portion 240 in contact with the inner surface 242 of the coronary artery 246. The central channel 248 through the stent is clear. Once the stent is in place and allowed to remain for some time, it has been observed that endothelial cells will grow and attach themselves to the inside surface 250 of the stent. They will grow over and incorporate the mesh structure within the structure of the coronary artery. In the event an excess of endothelial cells accumulate there, they can easily be resected mechanically, with a laser or by other suitable means.

Figure 9:
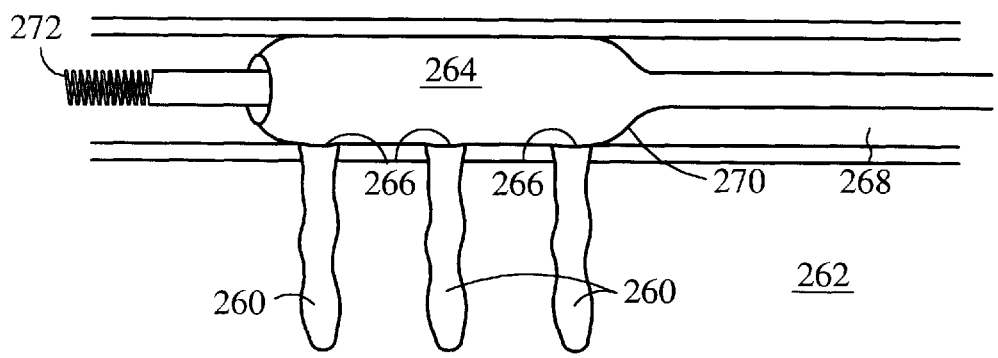
FIG. 9 is a graphic representation of a balloon device placed inside the coronary artery over the channel holes of a plurality of channels created using preferred embodiments of devices and methods of the present invention.

FIG. 9 is a graphic representation of a balloon device placed inside the coronary artery over the channel holes of a plurality of channels created using preferred embodiments of devices and methods of the present invention. In this preferred method, once the channels 260 are created in the myocardium tissue 262, a balloon device 264 is positioned directly over the perforations or channel holes 266 in the coronary artery 268. Angioplasty balloons have been used for years, and a similar type device would be useful here. It is a well known phenomenon that bleeding from tissue can be halted by the application of pressure over the wound site. In the present application, once the balloon is positioned, and inflated if necessary, the outer surface 270 of the balloon will seal the channel holes in the coronary artery. By applying this seal with some degree of pressure for approximately about 30 to 60 seconds, hemostasis will occur and the catheter balloon and associated devices can be withdrawn along with the guidewire 272 if no further channeling, visualization or other procedure is required.

Figure 10:
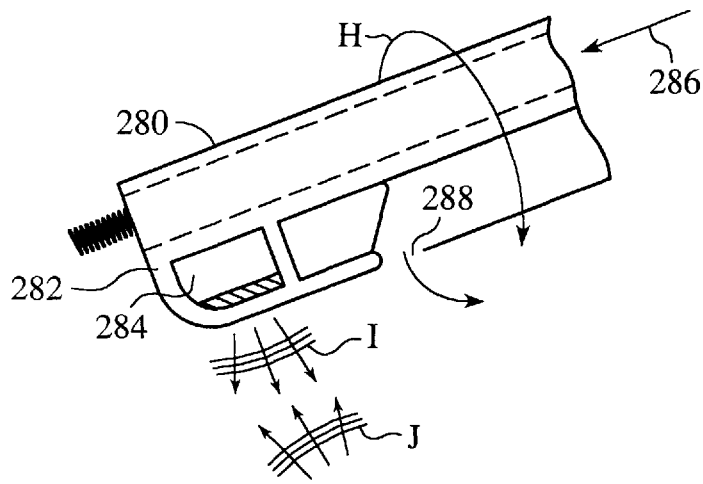
FIG. 10 is a graphical representation of a preferred embodiment of an interventional catheter device of the present invention having an ultrasound transceiver mounted at it's distal end, and method of use.

FIG. 10 is a graphical representation of a preferred embodiment of an interventional catheter device of the present invention having an ultrasound transceiver mounted at its distal end, and method of use. While the use of ultrasound is known in other medical modalities, its use for determining the angle of orientation of an interventional catheter device for performing ITMR or other similar surgical procedure is unknown heretofore. In this embodiment, the interventional catheter 280 has a distal end 282 which comprises an ultrasound transducer 284. Such transducer could be a piezoelectric crystal or some other ultrasound signal producing and signal receiving device or method. As the catheter device is torqued about its central axis 286 in the direction shown by arrow H, the ultrasound picture will show the orientation of the catheter device, and associated laser delivery means, relative to the coronary artery and the myocardium. This will reduce the risk of piercing a coronary artery on a side of the coronary not directly above the myocardium tissue, and causing excessive and unnecessary bleeding. The ultrasound transducer will emit sonic waves or another type of signal in a direction I away from the device will detect sonic waves or other signals propagating toward the transducer in the opposite direction J. The ultrasound transducer can create sound waves propagating in a direction through the laser delivery port 288 and the image detected by the transducer is essentially the image "seen" by the laser delivery means. It will be understood by those skilled in the art that the use of an ultrasound transducer may eliminate the need for a fluoroscope in some procedures and also reduce the patient's and the physician's exposure to harmful X-rays. It will further be understood by those skilled in the art that the transducer may also be made from a plurality of piezoelectric crystals arranged in a predetermined orientation or pattern, as would be optimized for creating a visual image and for differentiating rotational alignment of the laser delivery port and the myocardium.

Figure 11A:
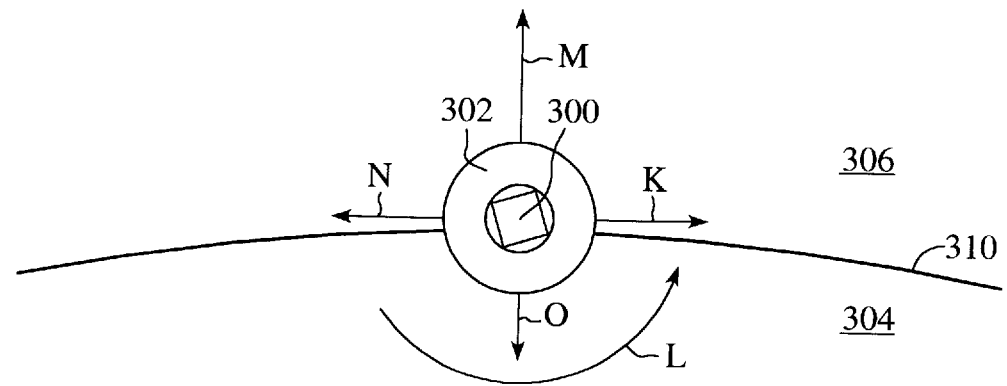
FIGS. 11A–E are graphical representations of ultrasound images made by a preferred embodiment of an interventional catheter device and method of use of the present invention.
Figure 11B:
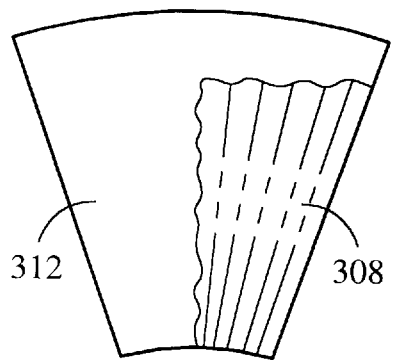
Figure 11C:
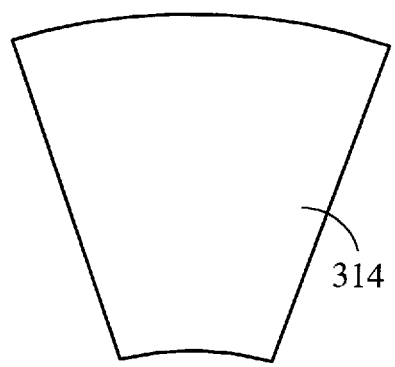
Figure 11D:
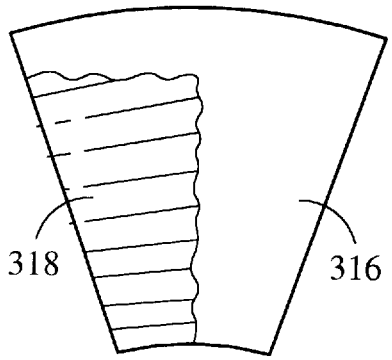
Figure 11E:
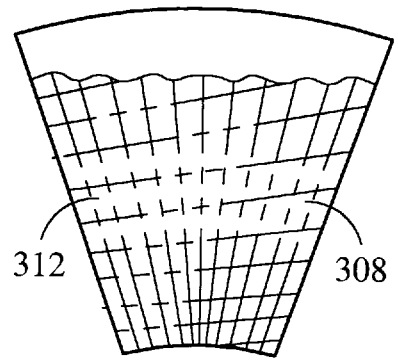

FIGS. 11A–E are graphical representations of ultrasound images made by a preferred embodiment of an interventional catheter device and method of use of the present invention. FIG. 11A is a graphic representation of a cross section of the interventional device 300 of the present invention disposed within the interior of the coronary artery 302. The coronary artery is shown partially contacting the myocardium 304 and partially exposed to the environment surrounding the heart 306, presumably the pericardium, a conical membranous sac in which the heart and the commencement of the great vessels are contained. Once the catheter device is placed in the coronary artery adjacent the myocardium tissue to be channeled into from within the coronary artery, an ultrasound image is taken. It might initially look like any of those representations in the subsequent 4 figures. If, for example, the distal end of the catheter device was oriented such that the laser delivery port and ultrasound transducer, both oriented in the same plane, were directed toward the interface between the outer atmosphere and the myocardium, in the direction K, an image such as that shown in FIG. 11B might be seen. In FIG. 11B an optically dense area 308 is shown to correspond to the portion of the myocardium just below the external surface 310 of the heart. A lighter appearing area 312 corresponds to the environment just above the surface of the heart. Both views are seen through the coronary wall. If the interventional catheter is rotated in direction L by about 90 degrees, the ultrasound transducer will direct waves toward and receive waves coming from the direction M. In this case, the image seen upon an ultrasound display would be similar to that shown in FIG. 11C. In the figure the light area 314 corresponds to the environment surrounding the heart. As the catheter device is rotated another 90 degrees to direct the ultrasound transducer and port opening toward the direction N, another split image is produced, the lighter area 316 and the darker area 318 correspond to the area above and the myocardium tissue, respectively. Finally, as the catheter device is rotated an additional 90 degrees in the same direction L, the image will reflect a view in about direction O, directly into the myocardium tissue. This is a preferred direction for delivering laser energy to create channels.

Figure 12A:
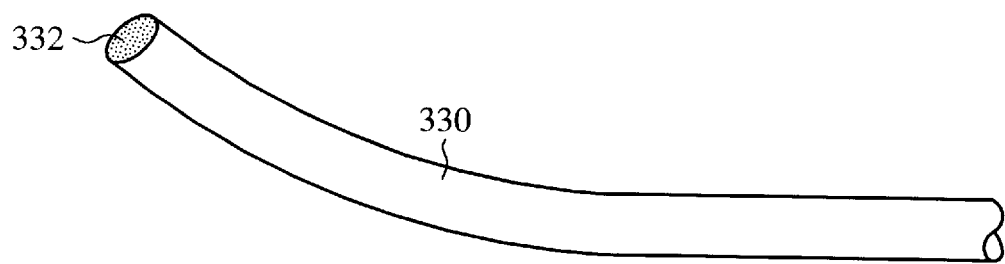
FIG. 12A is a perspective view of a preferred embodiment of a laser delivery fiber bundle spring member of the present invention.

FIG. 12A is a perspective view of a preferred embodiment of a laser delivery fiber bundle spring member of the present invention. Spring member 330 is bent near its distal end 332. The purpose of this wire is to impart a deflection at the distal end of a laser delivery means such as a fiber bundle. Spring members are well known in cardiac and other forms of catheterization. They are often referred to as spring guides, core wires, spring wires, etc. A guidewire with a J-tip is often used with tortuous vessels. One type of wire which is sometimes used in catheters is nitinol wire. Nitinol wire is used because it exhibits good steerability, torque transmission and bendability. Nitinol is known as a shape memory metal because it acts like a spring—once deformed it will maintain that shape until further permanently deformed. This shape memory characteristic operates in both a temperature mode as well as a super-elastic or spring mode—operating in the latter mode and bundled within a fiber matrix of a fiber bundle laser delivery device, the fiber bundle will be deflected in the direction of the nitinol wire once the distal end of the bundle is pushed through the laser delivery port at the end of the lumen of the catheter device of the present invention.

Figure 12B:
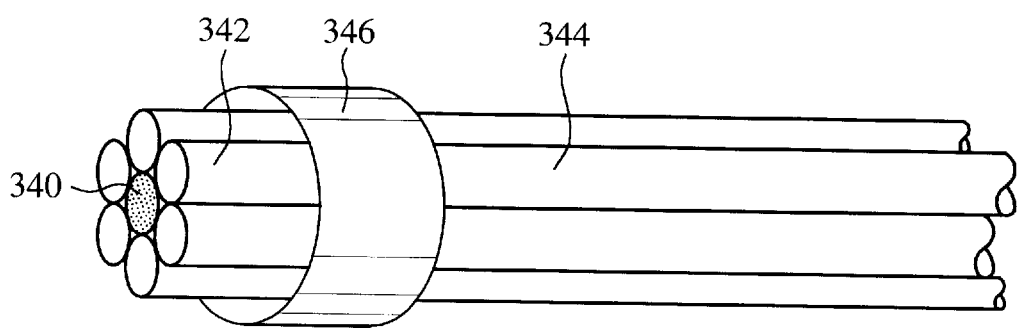
FIG. 12B is a perspective view of a preferred embodiment of a laser delivery fiber bundle with spring member of the present invention.

FIG. 12B is a perspective view of a preferred embodiment of a laser delivery fiber bundle with spring member of the present invention. The distal end 340 of the spring memory extends to adjacent the distal ends 342 of the fibers 344 of the laser delivery fiber bundle. The fiber is retained by some retaining means 346. This band or strap could also be replaced by adhesive, etc. In FIG. 12B, the laser delivery fiber bundle is essentially straight, i.e., without a bend at the distal end. The retaining means could also serve as a marker means. If a tantalum ring was placed at the same position, the ring would be radio-opaque on a radiograph, fluoroscope or other viewing means. In this manner the precise orientation and position of the distal ends of the fibers of the fiber bundle will be apparent to the surgeon and precise delivery of laser energy can be achieved.

Figure 12C:
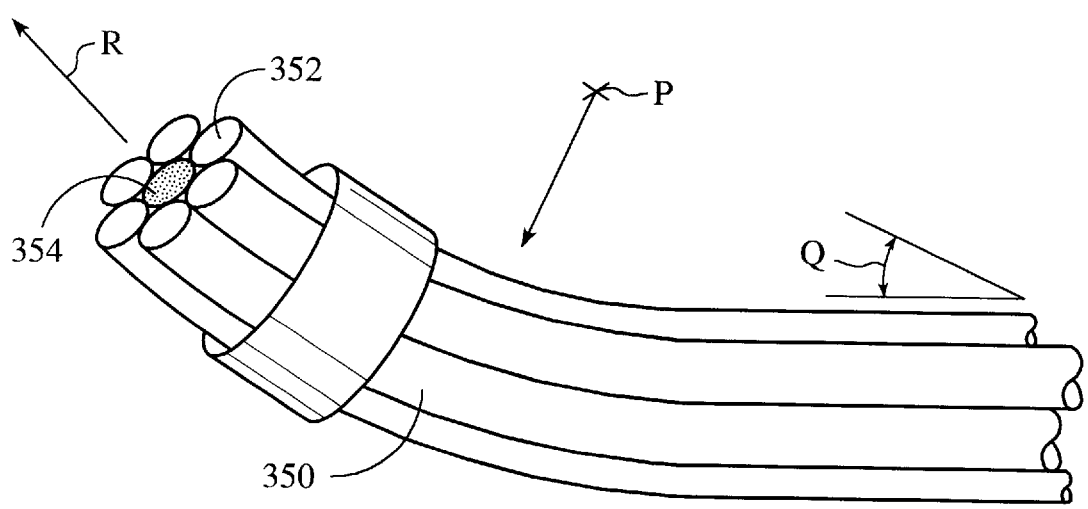
FIG. 12C is a perspective view of a preferred embodiment of a laser delivery fiber bundle with spring member of the present invention in a deflected position.

FIG. 12C is a perspective view of a preferred embodiment of a laser delivery fiber bundle with spring member of the present invention in a deflected position. In this embodiment, the fiber bundle 350 has a distal end 352 which delivers laser energy. Bundled within the fiber matrix is spring member 354. The spring member imparts a deflection of the fiber bundle, the deflection having a predetermined radius of curvature shown by vector P resulting in an angle of deflection Q. It will be understood that when the fiber bundle or other laser delivery means is inside the lumen of the catheter device, the confines of the lumen will prevent the bundle from being deflected at it's distal end. However, once the distal ends of the fibers extend through the end of the lumen or through the laser delivery port, the deflection will direct the distal ends of the laser delivery means in a predetermined angular direction in the direction R. In this way, delivery of laser energy can be effected at an angle to the central axis of the laser delivery means.

It will be understood that the above-described methods and devices for performing ITMR and other surgical procedures are but a few of the possible devices and methods contemplated and within the scope of this document. For example, it will be understood that the orientation of the channels created can be varied, i.e., they can be directed at angles other than perpendicular or normal to the surface of the heart from within the coronary artery. It will be understood that by making a single perforation in the coronary artery, laser energy can be directed into the myocardium tissue at more than one angle in a plane perpendicular to the central axis of the laser delivery means running inside the coronary artery. Along a length of a few centimeters, therefore, as many as 15 or 20 channels can be created extending radially from discrete points in the coronary artery. The procedure can be used to revascularize the heart muscle from either the left or the right ventricle, though it may be true that the myocardium tissue of the left ventricle is more frequently the site of ischemia or infarction.

The present invention is intended for use with any medical laser. In particular, the Holmium laser, including many of various different types known and available now or at any time, will be particularly suited to the present invention. However, any suitable laser source, pulsed or otherwise, could provide laser energy to the laser delivery means of the present invention for performing the method of the present invention. Likewise, the catheter and surgical equipment, including laser delivery means, referred to in the present document as well as that known and used in medicine and other disciplines today and in the future, will be included in the scope of this application.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true spirit and scope of the invention.

I claim:

1. An intracoronary transmyocardial revascularization catheter device comprising:
   a hub, having proximal and distal ends, housing at least one axially extending longitudinal channel, for delivery through the vasculature;
   a laser delivery system, having proximal and distal ends, housed in a first longitudinal channel, slidingly advancable and retractable through the first longitudinal channel;
   a laser delivery port adjacent the distal end of the hub, and in communication with the first longitudinal channel; and
   a laser delivery guide disposed in the laser delivery port placed at an angle to the axis of the first longitudinal channel, the laser delivery guide enabling the deflection of the distal end of the laser delivery system when the laser delivery system is in an advanced position, thereby enabling the delivery of laser energy through the wall of the coronary artery and into the myocardium.

2. The intracoronary transmyocardial revascularization catheter device of claim 1 wherein the laser delivery guide is comprised of a low friction coating.

3. The intracoronary transmyocardial revascularization catheter device of claim 2 wherein the low friction coating is paralyene.

4. The intracoronary transmyocardial revascularization catheter device of claim 1 wherein the laser delivery guide is comprised of a reflective surface coating.

5. The intracoronary transmyocardial revascularization catheter device of claim 1 further comprising a visualization system mounted at the distal end of the hub for creating a visual image for alignment of the laser delivery port.

6. The intracoronary transmyocardial revascularization catheter device of claim 5 wherein the visualization system comprises an ultrasound transducer.

7. The intracoronary transmyocardial revascularization catheter device of claim 6 wherein the ultrasound transducer comprises a piezoelectric crystal.

8. The intracoronary transmyocardial revascularization catheter device of claim 6 wherein the ultrasound transducer comprises a plurality of piezoelectric crystals arranged in a predetermined orientation.

9. The intracoronary transmyocardial revascularization catheter device of claim 5 wherein the visualization system comprises a radio opaque material.

10. The intracoronary transmyocardial revascularization catheter device of claim 1 wherein the laser delivery system comprises an optical fiber.

11. The intracoronary transmyocardial revascularization catheter device of claim 10 wherein the distal end of the laser delivery system has a curved profile.

12. The intracoronary transmyocardial revascularization catheter device of claim 10 wherein the distal end of the laser delivery system has a beveled profile.

13. The intracoronary transmyocardial revascularization catheter device of claim 10 wherein the distal end of the laser delivery system has a perforating shape for piercing the vasculature.

14. The intracoronary transmyocardial revascularization catheter device of claim 1 wherein the laser delivery system comprises an optical fiber bundle, having proximal and distal ends.

15. The intracoronary transmyocardial revascularization catheter device of claim 14 wherein the optical fiber bundle further includes a spring member, having proximal and distal ends, the distal end of the spring member extended adjacent to the distal end of the optical fiber bundle.

16. The intracoronary transmyocardial revascularization catheter device of claim 15 wherein the spring member is comprised of a shape memory metal.

17. The intracoronary transmyocardial revascularization catheter device of claim 16 wherein the spring member is comprised of nitinol.

18. The intracoronary transmyocardial revascularization catheter device of claim 15 further including a retaining member, for retaining the optical fiber bundle and spring member.

19. The intracoronary transmyocardial revascularization catheter device of claim 18 wherein the retaining member is comprised of a radio opaque material.

20. The intracoronary transmyocardial revascularization catheter device of claim 19 wherein the radio opaque material is comprised of tantalum.

21. The intracoronary transmyocardial revascularization catheter device of claim 1 further comprising a guidewire device slidably disposed in a second longitudinal channel of the hub.

22. The intracoronary transmyocardial revascularization catheter device of claim 1 further comprising a channel blocking device disposed in a third longitudinal channel of the hub, the channel blocking device enabling the application of pressure over a wound site.

23. The intracoronary transmyocardial revascularization catheter device of claim 22 wherein the channel blocking device comprises a stent.

24. The intracoronary transmyocardial revascularization catheter device of 22 wherein the channel blocking device comprises a balloon.

25. The intracoronary transmyocardial revascularization catheter device of claim 1 wherein the proximal end of the hub is comprised of a plurality of branched arms, each branched arm housing a singular longitudinal channel, each longitudinal channel continuous to the distal end of the hub.

26. The intracoronary transmyocardial revascularization catheter device of claim 25 wherein the proximal end of each branched arm of the hub further includes a blood loss seal device for preventing blood loss.

27. The intracoronary transmyocardial revascularization catheter device of claim 26 wherein the blood loss seal device is comprised of a deformable O-ring and threaded end cap.

28. An intracoronary transmyocardial revascularization catheter device comprising:
   a hub, having proximal and distal ends, housing at least one longitudinal channel, for delivery through the vasculature;
   a laser delivery system, having proximal and distal ends, housed in a first longitudinal channel, slidingly advancable and retractable through the first longitudinal channel;
   a laser delivery port adjacent the distal end of the hub, and in communication with the first longitudinal channel; and
   a laser delivery guide disposed in the laser delivery port, the laser delivery guide enabling the reflection of energy emitted by the laser delivery system onto the laser delivery guide and out the laser delivery port when the laser delivery system is in a retracted position, thereby enabling the delivery of laser energy through the wall of the coronary artery and into the myocardium.

29. The intracoronary transmyocardial revascularization catheter device of claim 28 wherein the laser delivery guide is comprised of a reflective surface coating.

30. The intracoronary transmyocardial revascularization catheter device of claim 28 wherein the laser delivery guide is comprised of a low friction coating.

31. The intracoronary transmyocardial revascularization catheter device of claim 30 wherein the low friction coating is paralyene.

32. The intracoronary transmyocardial revascularization catheter device of claim 28 further comprising a visualization system mounted at the distal end of the hub for creating a visual image for alignment of the laser delivery port.

33. The intracoronary transmyocardial revascularization catheter device of claim 32 wherein the visualization system comprises an ultrasound transducer.

34. The intracoronary transmyocardial revascularization catheter device of claim 33 wherein the ultrasound transducer comprises a piezoelectric crystal.

35. The intracoronary transmyocardial revascularization catheter device of claim 33 wherein the ultrasound transducer comprises a plurality of piezoelectric crystals arranged in a predetermined orientation.

36. The intracoronary transmyocardial revascularization catheter device of claim 32 wherein the visualization system comprises a radio opaque material.

37. The intracoronary transmyocardial revascularization catheter device of claim 28 wherein the laser delivery system comprises an optical fiber.

38. The intracoronary transmyocardial revascularization catheter device of claim 37 wherein the distal end of the laser delivery system has a curved profile.

39. The intracoronary transmyocardial revascularization catheter device of claim 37 wherein the distal end of the laser delivery system has a beveled profile.

40. The intracoronary transmyocardial revascularization catheter device of claim 37 wherein the distal end of the laser delivery system has a perforating shape for piercing the vasculature.

41. The intracoronary transmyocardial revascularization catheter device of claim 28 wherein the laser delivery system comprises an optical fiber bundle, having proximal and distal ends.

42. The intracoronary transmyocardial revascularization catheter device of claim 41 wherein the optical fiber bundle further includes a spring member, having proximal and distal ends, the distal end of the spring member extended adjacent to the distal end of the optical fiber bundle.

43. The intracoronary transmyocardial revascularization catheter device of claim 42 wherein the spring member is comprised of a shape memory metal.

44. The intracoronary transmyocardial revascularization catheter device of claim 43 wherein the spring member is comprised of nitinol.

45. The intracoronary transmyocardial revascularization catheter device of claim 42 further including a retaining member, for retaining the optical fiber bundle and spring member.

46. The intracoronary transmyocardial revascularization catheter device of claim 45 wherein the retaining member is comprised of a radio opaque material.

47. The intracoronary transmyocardial revascularization catheter device of claim 46 wherein the radio opaque material is comprised of tantalum.

48. The intracoronary transmyocardial revascularization catheter device of claim 28 further comprising a guidewire device slidably disposed in a second longitudinal channel of the hub.

49. The intracoronary transmyocardial revascularization catheter device of claim 28 further comprising a channel blocking device disposed in a third longitudinal channel of the hub, the channel blocking device enabling the application of pressure over a wound site.

50. The intracoronary transmyocardial revascularization catheter device of claim 49 wherein the channel blocking device comprises a stent.

51. The intracoronary transmyocardial revascularization catheter device of 49 wherein the channel blocking device comprises a balloon.

52. The intracoronary transmyocardial revascularization catheter device of claim 28 wherein the proximal end of the hub is comprised of a plurality of branched arms, each branched arm housing a singular longitudinal channel, each longitudinal channel continuous to the distal end of the hub.

53. The intracoronary transmyocardial revascularization catheter device of claim 52 wherein the proximal end of each branched arm of the hub further includes a blood loss seal device for preventing blood loss.

54. The intracoronary transmyocardial revascularization catheter device of claim 53 wherein the blood loss seal device is comprised of a deformable O-ring and threaded end cap.

\* \* \* \* \*